(12) United States Patent
Tung

(10) Patent No.: US 9,045,453 B2
(45) Date of Patent: Jun. 2, 2015

(54) SUBSTITUTED DIOXOPIPERIDINYL PHTHALIMIDE DERIVATIVES

(75) Inventor: Roger Tung, Lexington, MA (US)

(73) Assignee: Concert Pharmaceuticals, Inc., Lexington, MA (US)

( * ) Notice: Subject to any disclaimer, the term of this patent is extended or adjusted under 35 U.S.C. 154(b) by 408 days.

(21) Appl. No.: 13/107,873

(22) Filed: May 13, 2011

(65) Prior Publication Data

US 2011/0288126 A1    Nov. 24, 2011

Related U.S. Application Data

(63) Continuation-in-part of application No. PCT/US2009/006105, filed on Nov. 13, 2009.

(60) Provisional application No. 61/114,989, filed on Nov. 14, 2008, provisional application No. 61/368,221, filed on Jul. 27, 2010.

(51) Int. Cl.
*C07D 401/00* (2006.01)
*C07D 401/04* (2006.01)

(52) U.S. Cl.
CPC ........... *C07D 401/04* (2013.01); *C07B 2200/05* (2013.01)

(58) Field of Classification Search
CPC .................................................. C07D 401/04
USPC ....................................................... 514/323
See application file for complete search history.

(56) References Cited

U.S. PATENT DOCUMENTS

| | | | |
|---|---|---|---|
| 5,635,517 A * | 6/1997 | Muller et al. ................. | 514/323 |
| 6,221,335 B1 | 4/2001 | Foster | |
| 6,281,230 B1 * | 8/2001 | Muller et al. ................. | 514/323 |
| 6,440,710 B1 | 8/2002 | Keinan et al. | |
| 6,603,008 B1 | 8/2003 | Ando et al. | |
| 7,517,990 B2 | 4/2009 | Ito et al. | |
| 1,007,107 A1 | 3/2011 | Perni et al. | |
| 8,288,414 B2 * | 10/2012 | Czarnik ........................ | 514/323 |
| 2003/0096841 A1 | 5/2003 | Robarge et al. | |
| 2007/0082929 A1 | 4/2007 | Gant et al. | |
| 2007/0191432 A1 | 8/2007 | Tung | |
| 2007/0197695 A1 | 8/2007 | Potyen et al. | |
| 2008/0103122 A1 | 5/2008 | Veltri | |
| 2008/0108608 A1 | 5/2008 | Jones et al. | |
| 2008/0194617 A1 | 8/2008 | Tawaraishi et al. | |
| 2009/0069379 A1 | 3/2009 | Czarnik | |

FOREIGN PATENT DOCUMENTS

| | | | |
|---|---|---|---|
| WO | WO-95/26325 A2 | 10/1995 | |
| WO | WO-9803502 A1 | 1/1998 | |
| WO | 2006089150 A2 | 8/2006 | |
| WO | WO-2007118651 A1 | 10/2007 | |
| WO | 2010056344 A1 | 5/2010 | |
| WO | WO-2010056344 A1 | 5/2010 | |
| WO | 2010093605 A1 | 8/2010 | |
| WO | WO-2010093434 A1 | 8/2010 | |
| WO | WO-2011069608 A1 | 6/2011 | |
| WO | WO-2012015986 A2 | 2/2012 | |
| WO | 2012079022 A1 | 6/2012 | |
| WO | 2012079075 A1 | 6/2012 | |
| WO | 2013130849 A1 | 9/2013 | |

OTHER PUBLICATIONS

Wermuth the Practice of Med Chem 1996, pp. 203-237.*
Rhodes, Harold J., et al., Synthesis of 2,6-Dioxo-3-phthalimidopiperidine-3,4,4,5,5,-d, and 2,5-Dioxo-3-phthalimidopyrrolidine-3,4,4-d, from L-Deuterio-Glutamic Acid and L-Deuterio-Aspartic Acid, Journal of Pharmaceutical Sciences, 54(10):1440-1443, Oct. 1965.
He, Yihui, et al., Prospects for the Pharmacologica use of Heavy Water and Deuterium-Containing Drugs, Foreign Medical Sciences Epidemiology Lemology, 32(4):255-256; Aug. 2005.
International Search Report for PCT/US2011/064409, Mar. 23, 2012.
Written Opinion for PCT/US2011/064409, Mar. 23, 2012.
Tefferi, Ayalew, et al., "Pomalidomide is Active inthe Treatment of Anemia Associated with Myelofibrosis", Journal of Clinical Oncology, 27(27):4563, 2009.
Concert Pharmaceuticals, et al, Precision Deuterium Chemistry Backgrounder, http://www.webictation.org/5e81SGCn1, pp. 1-6, 2007.
Buteau, K.C., Deuteraed Drugs: Unexpectedly Nonobvious?, Journal of High Technology Law, Suffical University Law School, X(1):22-74; Jan. 2009.
International Search Report for PCT/US2011/064238, Feb. 27, 2012.
Written Opinion for PCT/US2011/064238, Feb. 27, 2012.
Ducho, C., et al., Synthesis of Regio-and Stereoselectivly Deuterium-Labelled Derivatives of L-Glutamate Semialdehyde for Studies on Carbapenem Biosynthesis, Organic & Biomolecular Chemistry, Royal Society of Chemistry, 7(11):2773, May 11, 2009.
Michalska, Danuta, The Raman and IR Spectra and Normal Coordinate Analysis of 3-(N-phenylacetylamino)-2,6-Piperidinedion e, Antineoplaston A10, the New Antitumor Drug, Spectrochimica Acta. Part A: Molecular and Biomolecular Spectroscopy, 49a(3):303-314, 1993.
Blomquist, Alfred, et al., Deuterated Amino Acids. III. Synthesis of DL-aspartic-2,3,3-d3 Acid, L- Glutamic-2,3,3,4,4-d5 Acid, Lasparagine-2,3,3-d3, and L-Glutamine-2,3,3,4,4-d5, Journal of Organic Chemistry, 31(12):4121-4127, 1966.

(Continued)

*Primary Examiner* — John Mabry
(74) *Attorney, Agent, or Firm* — McCarter & English, LLP; Steven G. Davis; Emily Dertz

(57) ABSTRACT

This invention relates to novel substituted dioxopiperidinyl phthalimide derivatives and pharmaceutically acceptable acid addition salts thereof. The invention also provides compositions comprising a compound of this invention and the use of such compositions in methods of treating diseases and conditions beneficially treated by an immunomodulatory agent.

23 Claims, No Drawing

(56) References Cited

OTHER PUBLICATIONS

International Search Report for PCT/US2013/028379, Aug. 2, 2013.
Written Opinion for PCT/US2013/028379, Aug. 2, 2013.
Chen, Nianhang, et al., Pharmacokinetics metabolism and exertion of [14C]-lenalidomide following oral administration in health male subjects, Cancer Chemother. Pharmacol., 69(3):789-787, 2011.
Extended European Search Report for Related European Application No. 09826438.5; May 18, 2012.
Baille, T. A., "The Use of Stable Isotopes in Pharmacological Research," *Pharmacological Reviews*, 33(2): 81-132 (1981).
Browne, T. R., "Stable Isotope Techniques in Early Drug Development: An Economic Evaluation," *J. Clin. Pharmacol.*, 38: 213-220 (1998).
Cherrah, Y., et al., "Study of Deuterium Isotope Effects on Protein Binding by Gas Chromatography/Mass Spectrometry. Caffeine and Deuterated Isotopomers," *Biomedical and Environmental Mass Spectrometry*, 14: 653-657 (1987).
Dyck, L. E., et al., "Effects of Deuterium Substitution on the Catabolism of β-Phenylethylamine: An In Vivo Study." *Journal of Neurochemistry*, 46(2): 399-404 (1986).
Foster, A. B., "Deuterium Isotope Effects in Studies of Drug Metabolism," *Trends in Pharmacological Sciences*, 5: 524-527 (1984).
Foster, A. B., "Deuterium Isotope Effects in the Metabolism of Drugs and Xenobiotics: Implications for Drug Design," *Advances in Drug Research*, 14: 1-40 (1985).
Gouyette, A., "Synthesis of Deuterium-labelled Elliptinium and its Use in Metabolic Studies," *Biomedical and Environmental Mass Spectrometry*, 15: 243-247 (1988).
Haskins, N. J., "The Application of Stable Isotopes in Biomedical Research," *Biomedical Mass Spectrometry*, 9(7): 269-277 (1982).
Honma S., et al., "The Metabolism of Roxatidine Acetate Hydrochloride," *Drug Metabolism and Disposition*, 15(4): 551-559 (1987).
Pieniaszek, H. J., et al., "Moricizine Bioavailability via Simultaneous, Dual, Stable Isotope Administration: Bioequivalence Implications," *J. Clin. Pharmacol*, 39: 817-825 (1999).
Tonn G. R., et al., "Simultaneous Analysis of Diphenhydramine and a Stable Isotope Analog ($^2H_{10}$) Diphenhydramine Using Capillary Gas Chromatography with Mass Selective Detection in Biological Fluids from Chronically Instrumented Pregnant Ewes," *Biological Mass Spectrometry*, 22: 633-642 (1993).
Wolen, R. L., "The Application of Stable Isotopes to Studies of Drug Bioavailability and Bioequivalence," *J. Clin. Pharmacol.*, 26: 419-424 (1986).
Fisher, M.B., et al., "The Complexities Inherent in Attempts to Decrease Drug Clearance by Blocking Sites of CYP-Mediated Metabolism," *Curr. Opin. Drug Discov. Devel.*, 9(1):101-109 (2006).
Kushner, D. J. et al., "Pharmacological Uses and Perspectives of Heavy Water and Deuterated Compounds," *Can. J. Physiol. Pharmacol.*, 77:69-88 (1999).
Center for Drug Evaluation and Research, Pharmacology/Toxicology Review and Evaluation for Revlimed ®; Apr. 7, 2005, 191 pp.
Reist, M., Chiral Inversion and Hydrolysis of Thalidomide: Mechanisms and Catalysis by Bases and Serum Albumin, and Chiral Stability of Teratogenic Metabolites; Chem. Res. Toxicol.; 11:1521-1528; 1998.
Maltais, F., In Vitro and In Vivo Isotope Effects with Hepatitis C Protease Inhibitors: Enhanced Plasma Exposure of Deuterated Telaprevir versus Telaprevir in Rats; J. Med. Chem. 52:7993-8001; 2009.
Yamamoto, T., et al., Synthesis and Configurational Stability of (S)- and (R)-deuteriothalidomides. Chem. Pharm. Bull; 58(1):110-112; 2010.
Science IP Search Results for Lenalidomide, CAS Chemcats database, 5pp., (2012).
Corral, L.G., et al., Differential Cytokine Modulation and T Cell Activtion by Two Distinct Classes of Thalidomide Analogues that are Potent Inhibitors of TNF-{alpha}; J. Immunol. 163:380-386; 1999.
Li, R., et al., Racemization of Vinylglycolate Catalyzed by Mandelate Racemase, J. Org. Chem., 60:3347-3351, 1995.

Eriksson, T., et al., Intravenous Formulations of the Enantiomers of Thalidomide: Pharmacokinetic and Initial Pharmacodynamic Characterization in Man; J. Pharm. Pharmacol., 52:807-817; 2000.
Eriksson, T., et al., Stereospecific Determination, Chiral Inversion In Vitro and Pharmacokinetics in Humans of the Enantiomers of Thalidomide; Chirality 7:44-51, 1995.
Eriksson, T., et al., Enantiomers of Thalidomide: Blood Distribution and the Influence of Serum Albumin on Chiral Inversion and Hydrolysis, Chirality, 10:223-228: 1998.
Pal, R., et al., Immunomodulatory Derivatives Induce PU.1 Down-Regulation, Myeloid Maturation Arrest, and Neutropenia, Blood, 115(3):605-614; Jan. 21, 2010.
Kumar, G., et al., Lenalidomide: In Vitro Evaluation of the Metabolism and Assessment of Cytochrome P450 Inhibition and Induction; Cancer Chemother Pharmacol; 5 pp., Nov. 23, 2008.
Highlights of Prescribing Information; REVLIMID®; 25 pp. 2005.
Richardson, P.G., et al., Lenalidomide in Multiple Myeloma; Expert Rev. Anticancer Ther. 6(8), 1165-1173, 2006.
Schreck, D.M., et al., Comparison of Racemic Albuterol and Levalbuterol in the Treatment of Acute Asthma in the ED. American Journal of Emergency Medicine; 23:842-847, 2005.
Stoschitzky, K., et al., Racemic (R,S)-propranolol Versus Half-Dosed Optically Pure (S)-Propranolol In Humans at Steady State: Hemodynamic Effects, Plasma Concentrations, and Influence on Thyroid Hormone Levels, Clin Pharmacol. Ther. 51:445-453; 1992.
Anderson, G., et al., Thalidomide Derivative CC-4047 Inhibits Osteoclast Formation by Down-Regulation of PU.1; Blood, 107(8):3098-3105, 2006.
International Search Report for PCT/US2011/045629, 4 pp, Mar. 15, 2012.
Written Opinion for PCT/US2011/045629; 5 pp, Mar. 15, 2012.
International Search Report of PCT/US09/06105; 2 pages, Jan. 25, 2010.
International Preliminary Report of Patentability for PCT/US09/06105; 4 pp, May 17, 2011.
Maltais, F., In Vitro and In Vivo Isotope Effects with Hepatitis C Protease Inhibitors: Enhanced Plasma Exposure of Deuterated Telaprevir versus Telaprevir in Rats; J. Med. Chem., Received Jul. 10, 2009.
Maltais, F., In Vitro and In Vivo Isotope Effects with Hepatitis C Protease Inhibitors: Enhanced Plasma Exposure of Deuterated Telaprevir versus Telaprevir in Rats: Abstract; http://pubs.acs.org/doi/abs/10.1021/jm90102; Nov. 6, 2009.
Highlights of Prescribing Information, REVLIMID®, 27 pp, Mar. 2012.
FDA Label, Revlimid-lenalidomide capsule; For Multiple Myeloma Myelodysplastic Syndrome and Mantle Cell Lymphoma; 47 pp; revised Sep. 2014.
"Lenalidomide in acute myeloid leukemia" from Clinical Studies Data accessed on Jan. 8, 2015.
Lenalidomide in acute myeloid leukemia: The NCT02126553 study from Clinical Studies Data accessed on Jan. 8, 2015.
Lenalidomide in amyloid light-chain amyloidosis from Clinical Studies Data accessed on Jan. 8, 2015.
Lenalidomide and dexamethasone in amyloidosis associated end-stage renal disease/dialysis: The NCT00091260 study from Clinical Studies Data accessed on Jan. 8, 2015.
Lenalidomide in follicular lymphoma: The NCT01180569 study from Clinical Studies Data accessed on Jan. 8, 2015.
Lenalidomide plus rituximab in follicular lymphoma from Clinical Studies Data accessed on Jan. 8, 2015.
Lenalidomide in chronic lymphocytic leukemia from Clinical Studies Data accessed on Jan. 8, 2015.
Lenalidomide in chronic lymphocytic leukemia from Clinical Studies Data accessed Jan. 8, 2015.
Lenalidomide in Hodgkin's lymphoma from Clinical Studies Data accessed on Jan. 8, 2015.
Lenalidomide in Hodgkin's lymphoma: The NCT00540007 study from Clinical Studies Data accessed on Jan. 8, 2015.
Lenalidomide in glioma: The NCT01222754 study from Clinical Studies Data accessed on Jan. 8, 2015.

(56) References Cited

OTHER PUBLICATIONS

Lenalidomide in diffuse large B-cell lymphoma from Clinical Studies Data accessed on Jan. 8, 2015.
Lenalidomide, rituximab, cyclophosphamide, vincristine, doxorubicin and prednisone in diffuse large B-cell/follicular lymphoma: The NCT00670358 study from Clinical Studies Data accessed on Jan. 8, 2015.
Lenalidomide in chronic myelomonocytic leukemia: The NCT01368757 study from Clinical Studies Data accessed on Jan. 8, 2015.
Lenalidomide in non-Hodgkin's lymphas from Clinical Studies Data accessed on Jan. 8, 2015.
Dexamethasone, lenalidomide, and rituximab in variable regimens in non-Hodgkin's B-cell lymphoma from Clinical Studies Data accessed on Jan. 8, 2015.
Lenalidomide Maintenance Therapy in Stage IIIB/IV Non-small Cell Lung Cancer from ClinicalTrials.gov accessed on Jan. 8, 2015.
Lenalidomide in T-cell non-Hodgkin's lymphoma: The NCT00322985 study from Clinical Studies Data accessed on Jan. 8, 2015.
Lenalidomide, romidepsin, and dexamethasone in variable regimens in Hodgkin's lymphoma/mature T-cell lymphoma/multiple myeloma: The RID; NCT01742793 study from Clinical Studies Data accessed on Jan. 8, 2015.
Lenalidomide in Waldenstrom's macroglobulinemia: The NCT02302469 study from Clinical Studies Data accessed on Jan. 8, 2015.
Lenalidomide, rituximab, cyclophosphamide and dexamethasone in non-Hodkin's lymphoma/Waldenstrom's macroglobulinemia accessed on Jan. 8, 2015.

* cited by examiner

US 9,045,453 B2

SUBSTITUTED DIOXOPIPERIDINYL PHTHALIMIDE DERIVATIVES

CROSS-REFERENCE TO RELATED APPLICATIONS

This application is a continuation-in-part of PCT Patent Application No. PCT/US2009/006105, filed Nov. 13, 2009, which in turn claims the benefit of U.S. Provisional Patent Application No. 61/114,989, filed Nov. 14, 2008. This application also claims the benefit of priority to U.S. Provisional Patent Application No. 61/368,221, filed Jul. 27, 2010. The contents of each of the foregoing applications are hereby incorporated by reference in their entirety.

BACKGROUND

Many current medicines suffer from poor absorption, distribution, metabolism and/or excretion (ADME) properties that prevent their wider use. Poor ADME properties are also a major reason for the failure of drug candidates in clinical trials. While formulation technologies and prodrug strategies can be employed in some cases to improve certain ADME properties, these approaches often fail to address the underlying ADME problems that exist for many drugs and drug candidates. One such problem is rapid metabolism that causes a number of drugs, which otherwise would be highly effective in treating a disease, to be cleared too rapidly from the body. A possible solution to rapid drug clearance is frequent or high dosing to attain a sufficiently high plasma level of drug. This, however, introduces a number of potential treatment problems such as poor patient compliance with the dosing regimen, side effects that become more acute with higher doses, and increased cost of treatment.

In some select cases, a metabolic inhibitor will be co-administered with a drug that is cleared too rapidly. Such is the case with the protease inhibitor class of drugs that are used to treat HIV infection. The FDA recommends that these drugs be co-dosed with ritonavir, an inhibitor of cytochrome P450 enzyme 3A4 (CYP3A4), the enzyme typically responsible for their metabolism (see Kempf, D. J. et al., Antimicrobial agents and chemotherapy, 1997, 41(3): 654-60). Ritonavir, however, causes adverse effects and adds to the pill burden for HIV patients who must already take a combination of different drugs. Similarly, the CYP2D6 inhibitor quinidine has been added to dextromethorphan for the purpose of reducing rapid CYP2D6 metabolism of dextromethorphan in a treatment of pseudobulbar affect. Quinidine, however, has unwanted side effects that greatly limit its use in potential combination therapy (see Wang, L et al., Clinical Pharmacology and Therapeutics, 1994, 56(6 Pt 1): 659-67; and FDA label for quinidine at www.accessdata.fda.gov).

In general, combining drugs with cytochrome P450 inhibitors is not a satisfactory strategy for decreasing drug clearance. The inhibition of a CYP enzyme's activity can affect the metabolism and clearance of other drugs metabolized by that same enzyme. CYP inhibition can cause other drugs to accumulate in the body to toxic levels.

A potentially attractive strategy for improving a drug's metabolic properties is deuterium modification. In this approach, one attempts to slow the CYP-mediated metabolism of a drug by replacing one or more hydrogen atoms with deuterium atoms. Deuterium is a safe, stable, non-radioactive isotope of hydrogen. Compared to hydrogen, deuterium forms stronger bonds with carbon. In select cases, the increased bond strength imparted by deuterium can positively impact the ADME properties of a drug, creating the potential for improved drug efficacy, safety, and/or tolerability. At the same time, because the size and shape of deuterium are essentially identical to those of hydrogen, replacement of hydrogen by deuterium would not be expected to affect the biochemical potency and selectivity of the drug as compared to the original chemical entity that contains only hydrogen.

Over the past 35 years, the effects of deuterium substitution on the rate of metabolism have been reported for a very small percentage of approved drugs (see, e.g., Blake, M I et al, J Pharm Sci, 1975, 64:367-91; Foster, A B, Adv Drug Res 1985, 14:1-40 ("Foster"); Kushner, D J et al, Can J Physiol Pharmacol 1999, 79-88; Fisher, M B et al, Curr Opin Drug Discov Devel, 2006, 9:101-09 ("Fisher")). The results have been variable and unpredictable. For some compounds deuteration caused decreased metabolic clearance in vivo. For others, there was no change in metabolism. Still others demonstrated increased metabolic clearance. The variability in deuterium effects has also led experts to question or dismiss deuterium modification as a viable drug design strategy for inhibiting adverse metabolism (see Foster at p. 35 and Fisher at p. 101).

The effects of deuterium modification on a drug's metabolic properties are not predictable even when deuterium atoms are incorporated at known sites of metabolism. Only by actually preparing and testing a deuterated drug can one determine if and how the rate of metabolism will differ from that of its non-deuterated counterpart. See, for example, Fukuto et al. (J. Med. Chem. 1991, 34, 2871-76). Many drugs have multiple sites where metabolism is possible. The site(s) where deuterium substitution is required and the extent of deuteration necessary to see an effect on metabolism, if any, will be different for each drug.

This invention relates to novel substituted dioxopiperidinyl phthalimide derivatives and pharmaceutically acceptable salts thereof. The invention also provides compositions comprising a compound of this invention and the use of such compositions in methods of treating diseases and conditions beneficially treated by an immunomodulatory agent.

Lenalidomide, chemically known as either 3-(4-amino-1,3-dihydro-1-oxo-2H-isoindol-2-yl)-2,6-piperidinedione or 3-(4-amino-1-oxo 1,3-dihydro-2H-isoindol-2-yl)piperidine-2,6-dione, and its pharmaceutically acceptable salts thereof are disclosed as immunomodulatory agents. Lenalidomide has been shown to inhibit the secretion of pro-inflammatory cytokines such as tumor necrosis factor alpha (TNF-α) and to increase the secretion of anti-inflammatory cytokines in animals and humans. Decreasing TNF-α levels is a valuable therapeutic strategy for the treatment of many inflammatory, infectious, immunological, and malignant diseases (PCT publication WO 98/03502). Lenalidomide has been demonstrated to be useful in the treatment of anemia due to myelodysplastic syndromes associated with a deletion 5q cytogenic abnormality, as well as in the treatment of multiple myeloma when used in combination with dexamethasone. (http://www.fda.gov/cder/foi/label/2006/021880s001.pdf).

Lenalidomide is also in clinical trials, alone or in combination with other therapeutic agents, for the treatment of Non-Hodgkins lymphoma; papillary and follicular thyroid carcinoma; prostate cancer; chronic lymphocytic leukemia, amyloidosis, complex regional pain syndrome Type I, malignant melanoma, radiculopathy, myelofibrosis, glioblastoma, gliosarcoma, malignant gliomas, myelogenous leukemia, refractory plasma cell neoplasm, chronic myelomonocytic leukemia, follicular lymphoma, ciliary body and chronic melanoma, iris melanoma, recurrent interocular melanoma, extraocular extension melanoma, solid tumors, T-cell lymphoma, erythroid lymphoma, monoblastic and monocytic leukemia; myeloid leukemia, brain tumor, meningioma, spinal cord tumors, thyroid cancers, mantle cell lymphoma, non-small cell lung cancer, ovarian cancer, prostate cancer, renal cell cancer, myelofibrosis, Burkitt's lymphoma, Hodgkin's lymphoma, large cell lymphoma, and Waldenstrom's macroglobulinemia.

Lenalidomide is associated with significant potential toxicities, which include human birth defects; neutropenia; thrombocytopenia; deep vein thrombosis; and pulmonary embolism. See (http://www.fda.gov/cder/foi/label/2006/021880s001.pdf). A majority of patients taking lenalidomide required a dose delay or reduction during clinical trials due to hematologic toxicities. No clinical studies were performed to assess the relationship between exposure and safety.

Despite the beneficial activities of lenalidomide, there is a continuing need for new compounds to treat the aforementioned diseases and conditions.

Definitions

The terms "ameliorate" and "treat" are used interchangeably and refer to therapeutic treatment. Both terms mean decrease, suppress, attenuate, diminish, arrest, or stabilize the development or progression of a disease (e.g., a disease or disorder delineated herein), lessen the severity of the disease or improve the symptoms associated with the disease.

"Disease" is meant any condition or disorder that damage or interferes with the normal function of a cell, tissue, or organ.

It will be recognized that some variation of natural isotopic abundance occurs in a synthesized compound depending upon the origin of chemical materials used in the synthesis. Thus, a preparation of lenalidomide will inherently contain small amounts of deuterated isotopologues. The concentration of naturally abundant stable hydrogen isotopes, notwithstanding this variation, is small and immaterial with respect to the degree of stable isotopic substitution of compounds of this invention. See for instance Wada, E and Hanba, Y, Seikagaku, 1994, 66: 15; Gannes, L Z et al, Comp Biochem Physiol A Mol Integr Physiol, 1998, 119: 725.

In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Also unless otherwise stated, when a position is designated specifically as "D" or "deuterium", the position is understood to have deuterium at an abundance that is at least 3340 times greater than the natural abundance of deuterium, which is 0.015% (i.e., at least 50.1% incorporation of deuterium).

The term "isotopic enrichment factor" as used herein means the ratio between the isotopic abundance and the natural abundance of a specified isotope.

In other embodiments, a compound of this invention has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

The term "isotopologue" refers to a species that differs from a specific compound of this invention only in the isotopic composition thereof.

The term "compound," when referring to a compound of this invention, refers to a collection of molecules having an identical chemical structure, except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this invention will depend upon a number of factors including the isotopic purity of deuterated reagents used to make the compound and the efficiency of incorporation of deuterium in the various synthesis steps used to prepare the compound. However, as set forth above the relative amount of such isotopologues in toto will be less than 49.9% of the compound. In other embodiments, the relative amount of such isotopologues in toto will be less than 47.5%, less than 40%, less than 32.5%, less than 25%, less than 17.5%, less than 10%, less than 5%, less than 3%, less than 1%, or less than 0.5% of the compound.

The invention also provides salts of the compounds of the invention.

A salt of a compound of this invention is formed between an acid and a basic group of the compound, such as an amino functional group, or a base and an acidic group of the compound, such as a carboxyl functional group. According to another preferred embodiment, the compound is a pharmaceutically acceptable acid addition salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric, hydrobromic, hydroiodic, sulfuric and phosphoric acid, as well as organic acids such as para-toluenesulfonic, salicylic, tartaric, bitartaric, ascorbic, maleic, besylic, fumaric, gluconic, glucuronic, formic, glutamic, methanesulfonic, ethanesulfonic, benzenesulfonic, lactic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylenesulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and the like salts. Preferred pharmaceutically acceptable acid addition salts include those formed with mineral acids such as hydrochloric acid and hydrobromic acid, and especially those formed with organic acids such as maleic acid.

The compounds of the present invention contain one or more asymmetric carbon atoms. As such, a compound of this invention can exist as the individual enantiomers as well a mixture of enantiomers. Accordingly, a compound of the present invention will include not only a racemic mixture, but also individual respective enantiomers substantially free of other enantiomers. The term "substantially free of other enantiomers" as used herein means less than 25% of other enantiomers, preferably less than 10% of other enantiomers, more preferably less than 5% of other enantiomers and most preferably less than 2% of other enantiomers are present. Methods of obtaining or synthesizing enantiomers are well known in the art and may be applied as practicable to final compounds or to starting material or intermediates.

Unless otherwise indicated when a disclosed compound is named or depicted by a structure without specifying the stereochemistry and has one or more chiral centers, it is understood to represent all possible stereoisomers of the compound.

The term "stable compounds", as used herein, refers to compounds which possess stability sufficient to allow manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"D" refers to deuterium. "Stereoisomer" refers to both enantiomers and diastereomers. "Tert", "t", and "t-" each refer to tertiary. "US" refers to the United States of America.

Throughout this specification, the terms "each Y," "each Z," and "each W" means, all "Y" groups (e.g., $Y^1$ and $Y^2$), all "Z" groups (e.g., $Z^1$, $Z^2$, $Z^3$, $Z^4$ and $Z^5$), and all "W" groups (e.g., $W^1$, $W^2$, $W^3$ and $W^4$), respectively.

Therapeutic Compounds

According to one embodiment, the present invention provides a compound of Formula I:

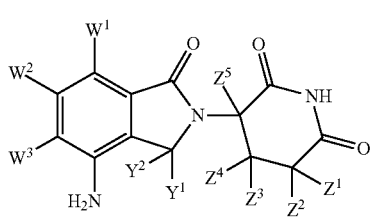

(I)

or a salt thereof, wherein:
each W is independently selected from hydrogen and deuterium;
each Y is independently selected from hydrogen and deuterium;
each Z is independently selected from hydrogen and deuterium; and
at least one W, one Y, or one Z is deuterium.

In one embodiment, $Z^5$ is deuterium. In one aspect of this embodiment, $Z^3$ and $Z^4$ are deuterium; $W^1$, $W^2$ and $W^3$ are simultaneously hydrogen or simultaneously deuterium; $Z^1$ and $Z^2$ are simultaneously hydrogen; and $Y^1$ and $Y^2$ are simultaneously hydrogen.

In one embodiment, $Z^5$ is deuterium. In one aspect of this embodiment, $Z^3$ and $Z^4$ are deuterium; $W^1$, $W^2$ and $W^3$ are simultaneously hydrogen or simultaneously deuterium; $Z^1$ and $Z^2$ are simultaneously hydrogen; and $Y^1$ and $Y^2$ are simultaneously deuterium.

In one embodiment, $Z^5$ is deuterium. In one aspect of this embodiment, $Z^1$, $Z^2$, $Z^3$ and $Z^4$ are simultaneously hydrogen; $W^1$, $W^2$ and $W^3$ are simultaneously hydrogen or simultaneously deuterium; and $Y^1$ and $Y^2$ are simultaneously hydrogen.

In another embodiment, $W^1$, $W^2$ and $W^3$ are the same. In one aspect of this embodiment $W^1$, $W^2$ and $W^3$ are simultaneously deuterium. In another aspect of this embodiment $W^1$, $W^2$ and $W^3$ are simultaneously hydrogen.

In another embodiment, each Z attached to a common carbon atom (e.g., $Z^1$ and $Z^2$; or $Z^3$ and $Z^4$) is the same. In one aspect of this embodiment, each member of at least one pair of Z attached to a common carbon atom is deuterium (e.g., at least $Z^1$ and $Z^2$ are deuterium; or at least $Z^3$ and $Z^4$ are deuterium). In another aspect of this embodiment, $Z^1$, $Z^2$, $Z^3$ and $Z^4$ are simultaneously deuterium. In another aspect of this embodiment, $Z^1$, $Z^2$, $Z^3$, $Z^4$ and $Z^5$ are simultaneously deuterium. In still another aspect, $Z^1$, $Z^2$, $Z^3$, $Z^4$ and $Z^5$ are simultaneously deuterium; and $W^1$, $W^2$ and $W^3$ are simultaneously hydrogen.

In yet another embodiment, each Y is simultaneously deuterium.

In another embodiment, the compound is selected from any one of the compounds set forth below:

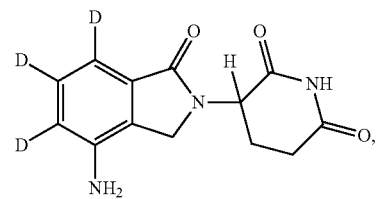

Compound 100

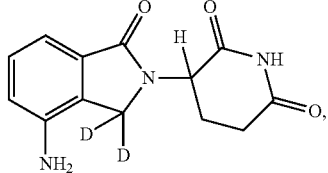

Compound 101

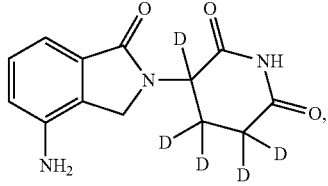

Compound 102

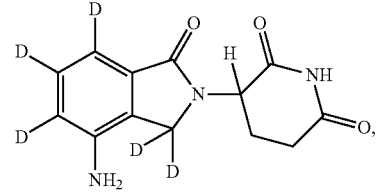

Compound 103

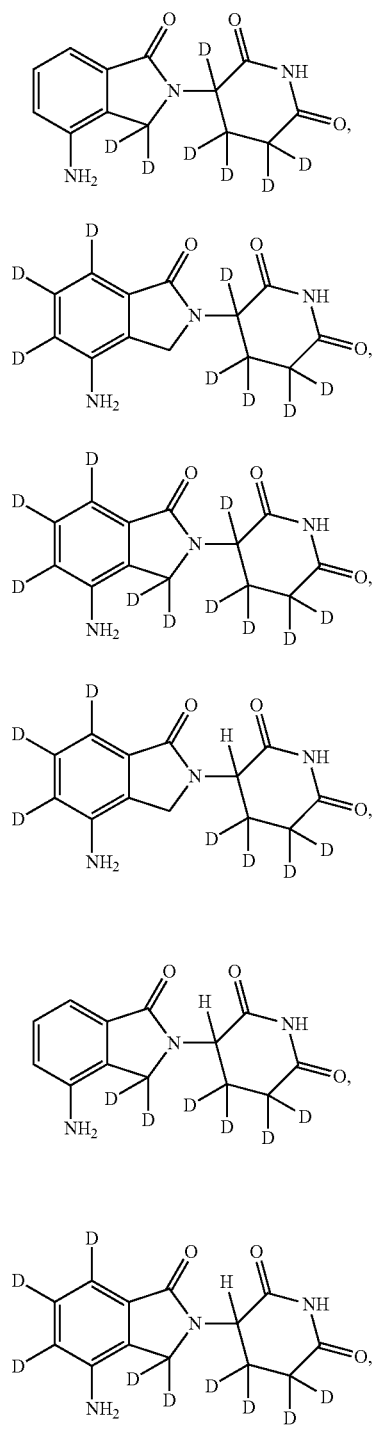

Compound 104
Compound 105
Compound 106
Compound 107
Compound 108
Compound 109

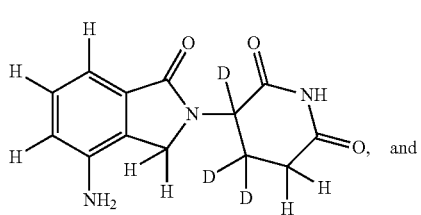

Compound 110

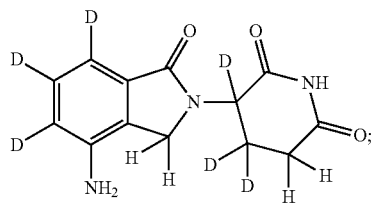

Compound 111 or a pharmaceutically acceptable salt thereof.

In another embodiment, the compound is selected from any one of the compounds set forth below:

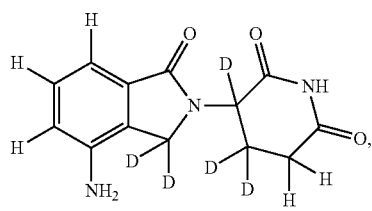

Compound 112

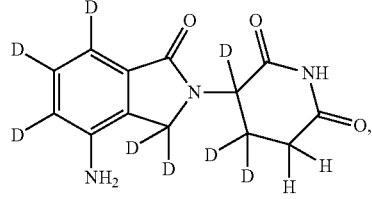

Compound 113

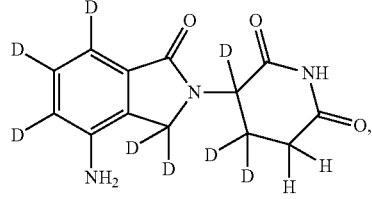

Compound 114

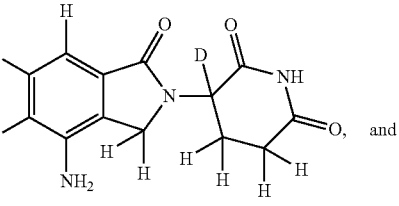

Compound 115

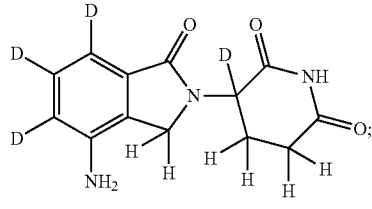

or a pharmaceutically acceptable salt thereof.

In another embodiment, the invention provides a compound of Formula I which is a compound of Formula Ia or Ib:

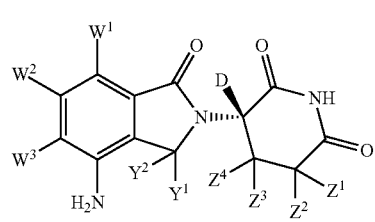

Ia

Ib

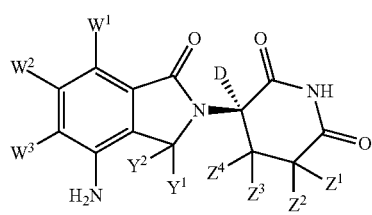

wherein W, Y, and Z are as defined above; or a pharmaceutically acceptable salt thereof.

The rate of epimerization for a compound of Formula Ia or Ib, as compared to the corresponding enantiomer of lenalidomide, can be readily measured using techniques well known to the skilled artisan. For example, pure samples of compounds of Formula Ia and Ib as well as pure samples of each enantiomer of lenalidomide can be isolated and analyzed using chiral HPLC. These pure samples can be dissolved to an appropriate concentration in an appropriate physiological buffer or bodily fluid or simulant thereof and monitored over time (for example, approximately every 5 minutes) using chiral HPLC, to assess the rate of epimerization.

In one embodiment of Formula Ia or Ib, $Z^3$ and $Z^4$ are deuterium; $W^1$, $W^2$ and $W^3$ are simultaneously hydrogen or simultaneously deuterium; $Z^1$ and $Z^2$ are simultaneously hydrogen; and $Y^1$ and $Y^2$ are simultaneously hydrogen.

In a further embodiment, the compound is selected from any one of the compounds set forth below:

Compound 102a

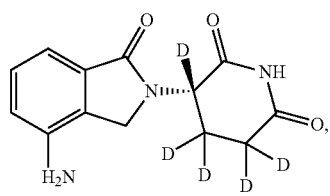

Compound 102b

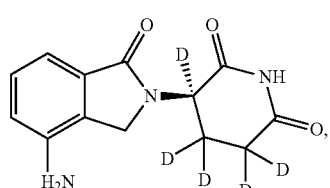

Compound 104a

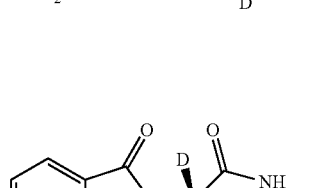

Compound 104b

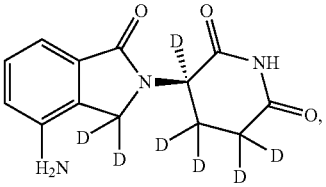

Compound 105a

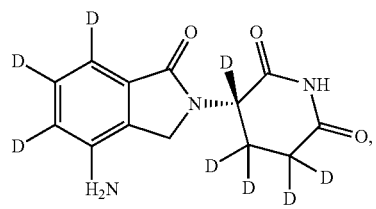

Compound 105b

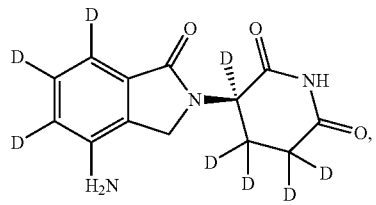

Compound 106a

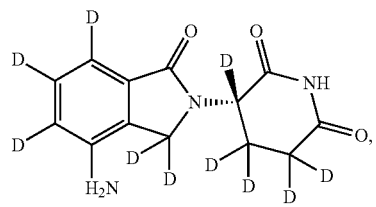

Compound 106b

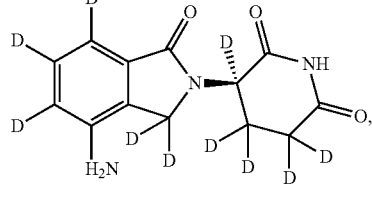

Compound 110a

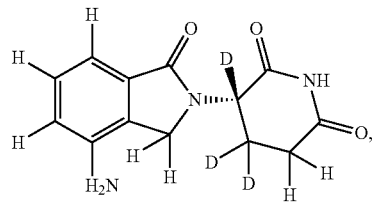

Compound 110b

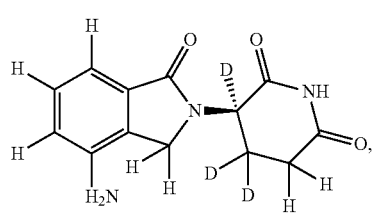

Compound 111a
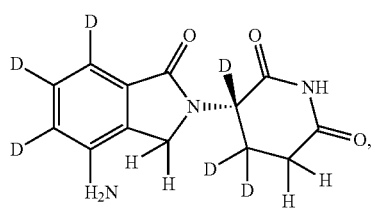

Compound 111b
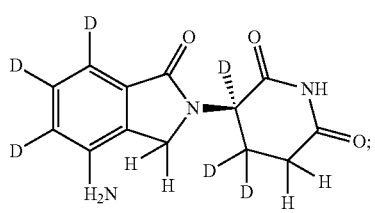

or a pharmaceutically acceptable salt thereof.

In another further embodiment, the compound is selected from any one of the compounds set forth below:

Compound 112a
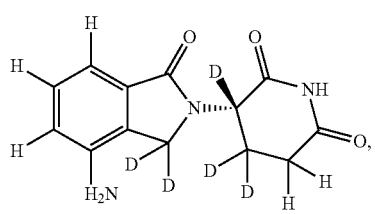

Compound 112b
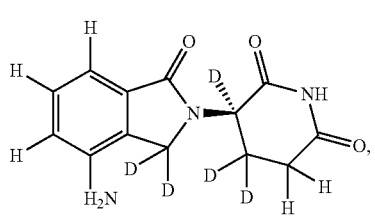

Compound 113a
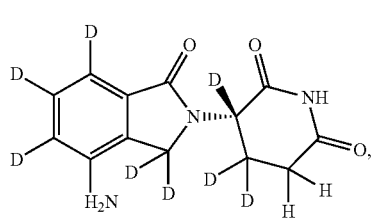

Compound 113b
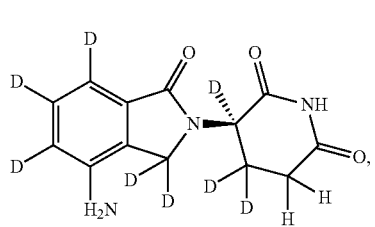

Compound 114a
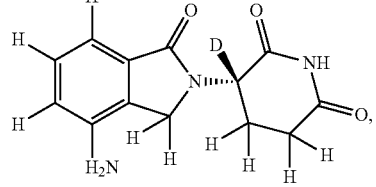

Compound 114b
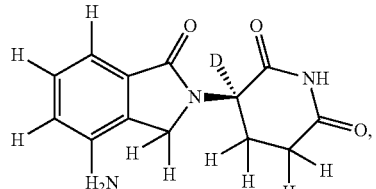

Compound 115a
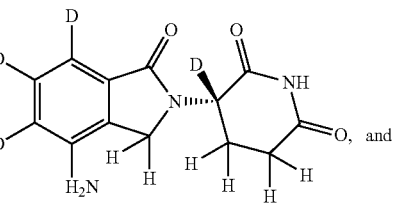, and

Compound 115b
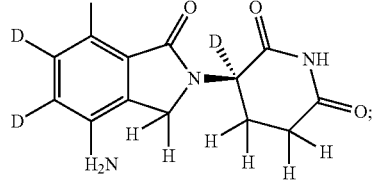

or a pharmaceutically acceptable salt thereof.

In one embodiment of Compound 102a or 102b, or a pharmaceutically acceptable salt thereof, the isotopic enrichment factor for the deuterium atom bonded to the carbon indicated with "$C_a$" in the figure below (shown for 102a) is at least 5500 (82.5% deuterium incorporation), at least 6000 (90% deuterium incorporation), or at least 6333.3 (95% deuterium incorporation);

the isotopic enrichment factor for the deuterium atoms bonded to the carbon indicated with "$C_b$" in the figure below is at least 5500 (82.5% deuterium incorporation), at least 6000 (90% deuterium incorporation), or at least 6333.3 (95% deuterium incorporation);

and the isotopic enrichment factor for the deuterium atom bonded to the carbon indicated with "$C_c$" in the figure below is at least 5500 (82.5% deuterium incorporation), at least 6000 (90% deuterium incorporation), or at least 6333.3 (95% deuterium incorporation):

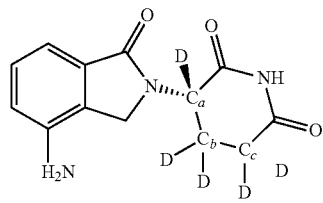

wherein any atom not designated as deuterium is present at its natural isotopic abundance.

In one embodiment of Compound 104a or 104b, or a pharmaceutically acceptable salt thereof, the isotopic enrichment factor for the deuterium atom bonded to the carbon indicated with "$C_a$" in the figure below (shown for 104a) is at least 5500 (82.5% deuterium incorporation), at least 6000 (90% deuterium incorporation), or at least 6333.3 (95% deuterium incorporation);

the isotopic enrichment factor for the deuterium atoms bonded to the carbon indicated with "$C_b$" in the figure below is at least 5500 (82.5% deuterium incorporation), at least 6000 (90% deuterium incorporation), or at least 6333.3 (95% deuterium incorporation);

the isotopic enrichment factor for the deuterium atom bonded to the carbon indicated with "$C_c$" in the figure below is at least 5500 (82.5% deuterium incorporation), at least 6000 (90% deuterium incorporation), or at least 6333.3 (95% deuterium incorporation);

and the isotopic enrichment factor for the deuterium atom bonded to the carbon indicated with "$C_d$" in the figure below is at least 5500 (82.5% deuterium incorporation), at least 6000 (90% deuterium incorporation), or at least 6333.3 (95% deuterium incorporation);

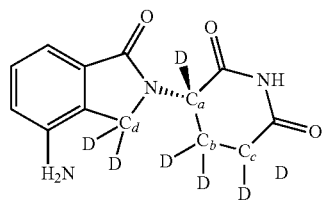

wherein any atom not designated as deuterium is present at its natural isotopic abundance.

In one embodiment of Compound 110a or 110b, or a pharmaceutically acceptable salt thereof, the isotopic enrichment factor for the deuterium atom bonded to the carbon indicated with "$C_a$" in the figure below (shown for 110a) is at least 5500 (82.5% deuterium incorporation), at least 6000 (90% deuterium incorporation), or at least 6333.3 (95% deuterium incorporation);

and the isotopic enrichment factor for the deuterium atoms bonded to the carbon indicated with "$C_b$" in the figure below is at least 5500 (82.5% deuterium incorporation), at least 6000 (90% deuterium incorporation), or at least 6333.3 (95% deuterium incorporation):

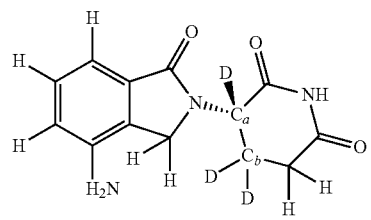

wherein any atom not designated as deuterium is present at its natural isotopic abundance.

In one embodiment of Compound 111a or 111b, or a pharmaceutically acceptable salt thereof, the isotopic enrichment factor for the deuterium atom bonded to the carbon indicated with "$C_a$" in the figure below (shown for 111a) is at least 5500 (82.5% deuterium incorporation), at least 6000 (90% deuterium incorporation), or at least 6333.3 (95% deuterium incorporation);

the isotopic enrichment factor for the deuterium atoms bonded to the carbon indicated with "$C_b$" in the figure below is at least 5500 (82.5% deuterium incorporation), at least 6000 (90% deuterium incorporation), or at least 6333.3 (95% deuterium incorporation);

and the isotopic enrichment factor for the deuterium atom bonded to each carbon indicated with "$C_e$" in the figure below is at least 5500 (82.5% deuterium incorporation), at least 6000 (90% deuterium incorporation), or at least 6333.3 (95% deuterium incorporation);

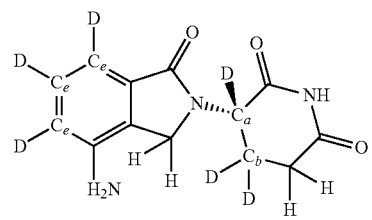

wherein any atom not designated as deuterium is present at its natural isotopic abundance.

In one embodiment of Compound 114a or 114b or a pharmaceutically acceptable salt thereof, the isotopic enrichment factor for the deuterium atom bonded to the carbon indicated with "$C_a$" in the figure below (shown for 114a) is at least 5500 (82.5% deuterium incorporation), at least 6000 (90% deuterium incorporation), or at least 6333.3 (95% deuterium incorporation):

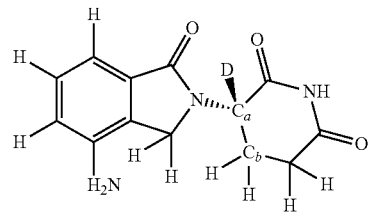

wherein any atom not designated as deuterium is present at its natural isotopic abundance.

A hemihydrate of lenalidomide has been described in U.S. Pat. No. 7,465,800. Accordingly, in one embodiment, the invention is directed to a hemihydrate of a compound of formula I, such as a crystalline hemihydrate, including a hemihydrate or crystalline hemihydrate of compounds 100, 101, 102, 103, 104, 105, 106, 107, 108, 109, 110, 111, 112, 113, 114, and 115.

In another set of embodiments, any atom not designated as deuterium in any of the embodiments set forth above is present at its natural isotopic abundance.

The synthesis of compounds disclosed herein can be readily achieved by synthetic chemists of ordinary skill by reference to the Exemplary Synthesis and Examples disclosed herein. Relevant procedures and intermediates are disclosed, for instance, in U.S. Pat. No. 5,635,517 and US Patent Application 2006052609, in addition to Muller, G W et al., Bioorg Med Chem Lett, 1999, 9(11): 1625.

Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure.

Exemplary Synthesis

A convenient method for synthesizing compounds of Formula I is depicted in Schemes 1 and 2.

Scheme 1. Synthesis of an Appropriately Deuterated 3-Aminopiperidine-2,6 dione (13).

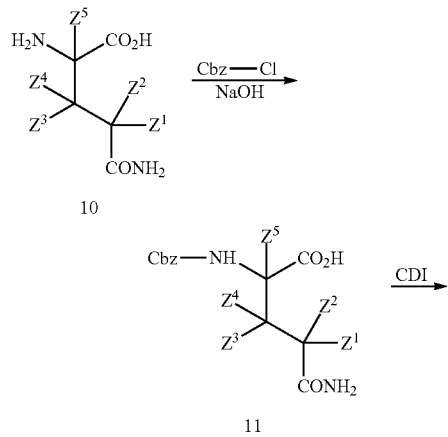

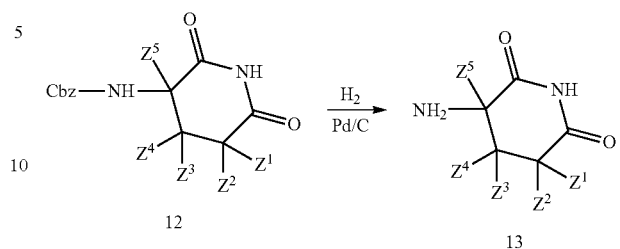

As shown in Scheme 1, an appropriately deuterated d,l-glutamine 10 is reacted with Cbz-chloride to yield the carbamate 11, which is then cyclized with 1,1'-carbonyldiimidazole (CDI) to yield 12. The carbamate protecting group is then removed from 12 by hydrogenolysis to provide the appropriately deuterated 3-aminopiperidine-2,6-dione 13. This amine is then used as shown in Scheme 2 to produce a compound of Formula I.

Scheme 2. Synthesis of a Compound or Formula I.

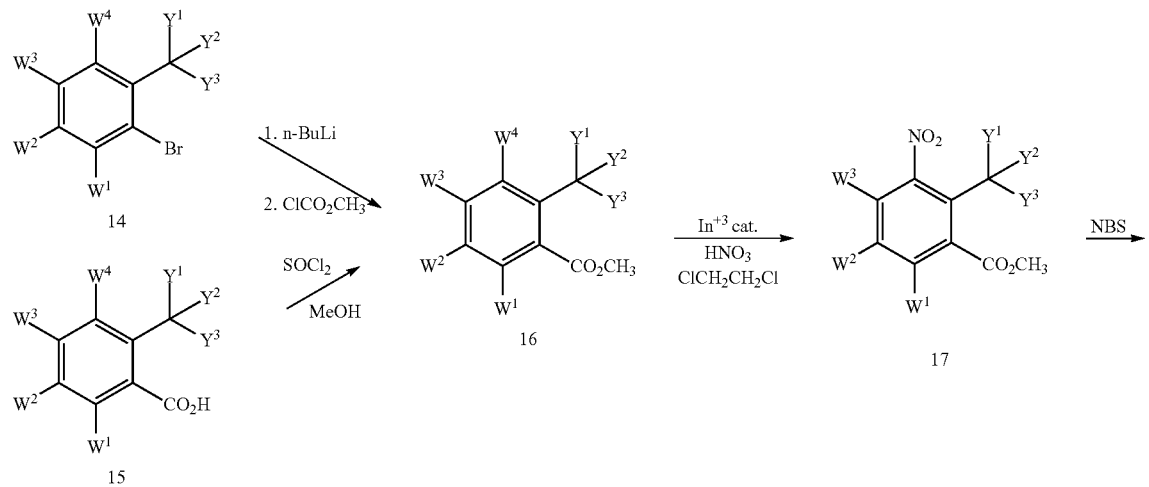

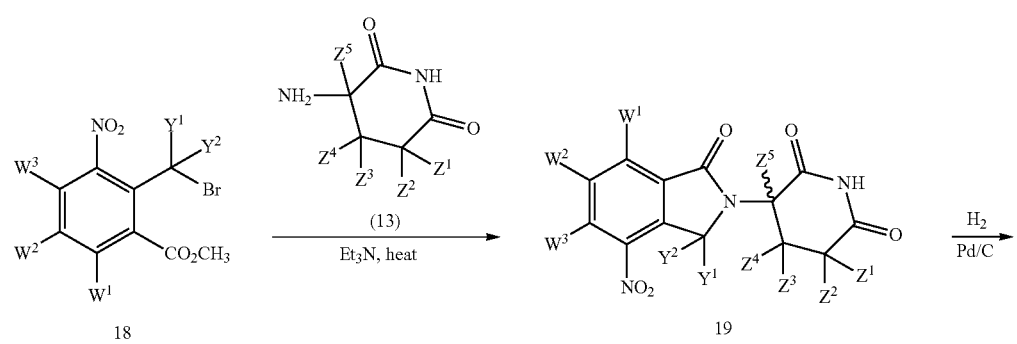

-continued

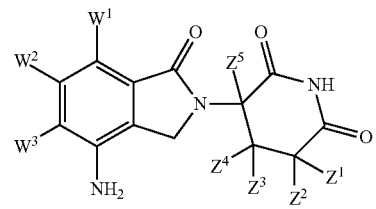

Formula I

As depicted in Scheme 2 for the preparation of a compound of Formula I, an appropriately deuterated 1-bromo-2-methylbenzene 14 is lithiated with n-butyl lithium followed by reaction with methyl chloroformate to provide ester 16. Alternatively, ester 16 can be obtained by treating an appropriately deuterated 2-methylbenzoic acid with sulfonyl chloride in methanol. The ester 16 is nitrated with nitric acid in dichloroethane with an Indium catalyst to provide the nitro compound 17, which is then converted to the benzylic halide 18 by treatment with N-bromosuccinimide. Reaction of the benzylic halide 18 with an appropriately deuterated 3-aminopiperidine-2,6-dione 13 in the presence of triethylamine and heat yields the cyclized nitro compound 19, which is then converted to a compound of Formula I by hydrogenation using a Pd/C catalyst. If desired, the R and S enantiomers of a compound of Formula I can then be separated by chiral HPLC in a manner similar to that known for related compounds in the IMiD class of drugs. Examples of this type of chiral HPLC enantiomer separation are found in Sembongi, K. et al., Biological and Pharmaceutical Bulletin, 2008, 31(3): 497-500; Murphy-Poulton, S. F. et al., Journal of Chromatography, B: Analytical Technologies in the Biomedical and Life Sciences, 2006, 831(1-2): 48-56; Eriksson, T. et al., Journal of Pharmacy and Pharmacology, 2000, 52(7): 807-817; Eriksson, T. et al., Chirality, 1998, 10(3): 223-228; Reepmeyer, J. C. et al., Chirality, 1996, 8(1): 11-17; Aboul-Enein, H. Y. et al., Journal of Liquid Chromatography, 1991, 14(4): 667-73; and Teo, S. K. et al., Chirality, 2003, 15(4): 348-351.

The specific approaches and compounds shown above are not intended to be limiting. The chemical structures in the schemes herein depict variables that are hereby defined commensurately with chemical group definitions (moieties, atoms, etc.) of the corresponding position in the compound formulae herein, whether identified by the same variable name (i.e., $R^1$, $R^2$, $R^3$, etc.) or not. The suitability of a chemical group in a compound structure for use in the synthesis of another compound is within the knowledge of one of ordinary skill in the art.

Additional methods of synthesizing compounds of the formulae herein and their synthetic precursors, including those within routes not explicitly shown in Schemes herein, are within the means of chemists of ordinary skill in the art. Synthetic chemistry transformations and protecting group methodologies (protection and deprotection) useful in synthesizing the applicable compounds are known in the art and include, for example, those described in R. Larock, *Comprehensive Organic Transformations*, VCH Publishers (1989); T. W. Greene and P. G. M. Wuts, *Protective Groups in Organic Synthesis*, $3^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

Combinations of substituents and variables envisioned by this invention are only those that result in the formation of stable compounds.

Compositions

The invention also provides pyrogen-free pharmaceutical compositions comprising an effective amount of a compound of Formula I (e.g., including any of the formulae herein), or a pharmaceutically acceptable salt thereof; and an acceptable carrier. The carrier(s) must be "acceptable" in the sense of being compatible with the other ingredients of the formulation and, in the case of a pharmaceutically acceptable carrier, not deleterious to the recipient thereof in amounts typically used in medicaments.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

If required, the solubility and bioavailability of the compounds of the present invention in pharmaceutical compositions may be enhanced by methods well-known in the art. One method includes the use of lipid excipients in the formulation. See "Oral Lipid-Based Formulations Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this invention optionally formulated with a poloxamer, such as LUTROL™ and PLURONIC™ (BASF Corporation), or block copolymers of ethylene oxide and propylene oxide. See U.S. Pat. No. 7,014,866; and United States patent publications 20060094744 and 20060079502.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets and sustained release capsules, and in liposomes, and may be prepared by any methods well known in the art of pharmacy. See, for example, Remington: The Science and Practice of Pharmacy, Lippincott Williams and Wilkins, Baltimore, Md. (20th ed. 2000).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers or both, and then if necessary shaping the product.

In certain preferred embodiments, the compound is administered orally. Compositions of the present invention suitable for oral administration may be presented as discrete units such as capsules, sachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion, or packed in liposomes and as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Such administration is known to be effective with erectile dysfunction drugs: Rabinowitz J D and Zaffaroni A C, U.S. Pat. No. 6,803,031, assigned to Alexza Molecular Delivery Corporation.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches and iontophoretic administration are also included in this invention.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

Thus, according to yet another embodiment, the compounds of this invention may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein. In one preferred embodiment, a compound of Formula I is formulated into a hydrogel for delivery to the eye as described in United States Patent Publication US2005074497.

According to another embodiment, the invention provides a method of coating an implantable medical device comprising the step of contacting said device with the coating composition described above. It will be obvious to those skilled in the art that the coating of the device will occur prior to implantation into a mammal.

According to another embodiment, the invention provides a method of impregnating an implantable drug release device comprising the step of contacting said drug release device with a compound or composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with a compound or a composition comprising a compound of this invention, such that said compound is therapeutically active.

According to another embodiment, the invention provides an implantable drug release device impregnated with or containing a compound or a composition comprising a compound of this invention, such that said compound is released from said device and is therapeutically active.

Where an organ or tissue is accessible because of removal from the patient, such organ or tissue may be bathed in a medium containing a composition of this invention, a composition of this invention may be painted onto the organ, or a composition of this invention may be applied in any other convenient way.

In another embodiment, a composition of the present invention further comprises a second therapeutic agent. The second therapeutic agent includes any compound or therapeutic agent known to have or that demonstrates advantageous properties when administered with an immunomodulator, an anti-angiogenic or an anti-neoplastic agent. Such agents are described in detail in U.S. Pat. No. 5,635,517, as well as in PCT patent publications WO2005097125, WO2005055929, WO2004041190, WO2006060507, WO2006058008, WO2006053160, WO2006044178, WO2004100953, WO2006089150, WO2006036892, WO2006018182, WO2005082415, WO2005048942, WO2005042558, WO2005035714 and WO2005027842; and in United States Patent publications US2005100529, US2006030594, US2005143344 and US2006079461, each of the foregoing of which describes second therapeutic agents that may be combined with lenalidomide.

In one embodiment, the second therapeutic agent is an agent useful in the treatment of a disease or condition selected from myelodysplastic syndromes, multiple myeloma, Non-Hodgkins lymphoma; papillary and follicular thyroid carcinoma; prostate cancer; chronic lymphocytic leukemia, amyloidosis, complex regional pain syndrome Type I, malignant melanoma, radiculopathy, myelofibrosis, glioblastoma, gliosarcoma, malignant gliomas, myelogenous leukemia, refractory plasma cell neoplasm, chronic myelomonocytic leukemia, follicular lymphoma, ciliary body and chronic melanoma, iris melanoma, recurrent interocular melanoma, extraocular extension melanoma, solid tumors, T-cell lymphoma, erythroid lymphoma, monoblastic and monocytic leukemia; myeloid leukemia, brain tumor, meningioma, spinal cord tumors, thyroid cancers, mantle cell lymphoma, non-small cell lung cancer, ovarian cancer, prostate cancer, renal cell cancer, myelofibrosis, Burkitt's lymphoma, Hodgkin's lymphoma, large cell lymphoma, or Waldenstrom's macroglobulinemia.

In another embodiment, the second therapeutic agent is an agent useful in the treatment of a disease or condition selected from dysfunctional sleep, hemoglobinopathy, anemia, macular degeneration, atherosclerosis, restenosis, pain, immunodeficiencies, CNS injury and related symptoms, CNS disorders, parasitic disease, or asbestos-related disease.

Even more preferably the second therapeutic agent co-formulated with a compound of this invention is an agent useful in the treatment of myelodysplastic syndromes or multiple myeloma.

In another preferred embodiment, the second therapeutic agent is selected from aldesleukin; a p38 MAP kinase inhibitor such as disclosed in US2006079461; a 24-hydroxylase inhibitor such as disclosed in WO2006036892; an aminopteridinone such as disclosed in WO2006018182; an IGF-R inhibitor such as disclosed in WO2005082415; a COX-2 inhibitor such as disclosed in WO2005048942; a nucleobase oligomer such as disclosed in WO2005042558; a chlorpromazine compound such as disclosed in WO2005027842.

In yet another preferred embodiment, the second therapeutic agent is selected from pemetrexed, topotecan, doxorubicin, bortezomib, gemcitabine, dacarbazine, dexamethasone, biaxin, doxil, vincristine, decadron, azacitidine, rituximab, prednisone, docetaxel, melphalan, or combinations thereof.

In another embodiment, the invention provides separate dosage forms of a compound of this invention and a second therapeutic agent that are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, the compound of the present invention is present in an effective amount. As used herein, the term "effective amount" refers to an amount which, when administered in a proper dosing regimen, is sufficient to reduce or ameliorate the severity, duration or progression of the disorder being treated, prevent the advancement of the disorder being treated, cause the regression of the disorder being treated, or enhance or improve the therapeutic effect(s) of another therapy.

The interrelationship of dosages for animals and humans (based on milligrams per meter squared of body surface) is described in Freireich et al., 1966, Cancer Chemother Rep, 50: 219. Body surface area may be approximately determined from height and weight of the patient. See, e.g., Scientific Tables, Geigy Pharmaceuticals, Ardsley, N.Y., 1970, 537. An effective amount of a compound of this invention can range from about 0.005 mg/kg to about 200 mg/kg, more preferably 0.01 mg/kg to about 100 mg/kg, more preferably 0.05 mg/kg to about 60 mg/kg.

Effective doses will also vary, as recognized by those skilled in the art, depending on the diseases treated, the severity of the disease, the route of administration, the sex, age and general health condition of the patient, excipient usage, the possibility of co-usage with other therapeutic treatments such as use of other agents and the judgment of the treating physician. For example, guidance for selecting an effective dose can be determined by reference to the prescribing information for lenalidomide.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al, eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

It is expected that some of the second therapeutic agents referenced above will act synergistically with the compounds of this invention. When this occurs, its will allow the effective dosage of the second therapeutic agent and/or the compound of this invention to be reduced from that required in a monotherapy. This has the advantage of minimizing toxic side effects of either the second therapeutic agent of a compound of this invention, synergistic improvements in efficacy, improved ease of administration or use and/or reduced overall expense of compound preparation or formulation.

Methods of Treatment

According to another embodiment, the invention provides a method of treating a disease that is beneficially treated by lenalidomide in a patient in need thereof, comprising the step of administering to the patient an effective amount of a compound or a composition of this invention. Such diseases are well known in the art and are disclosed in U.S. Pat. No. 5,635,517, as well as in PCT patent publications WO2005097125, WO2005055929, WO2004041190, WO2006060507, WO2006058008, WO2006053160, WO2005044178, WO2004100953, WO2006089150, WO2006036892, WO2006018182, WO2005082415, WO2005048942, WO2005042558, WO2005035714 and WO2005027842; and in United States Patent publications US2005100529, US2006030594, US2005143344 and US2006079461.

In one preferred embodiment, the disease or condition is selected from myelodysplastic syndromes, multiple myeloma, Non-Hodgkins lymphoma; papillary and follicular thyroid carcinoma; prostate cancer; chronic lymphocytic leukemia, amyloidosis, complex regional pain syndrome Type I, malignant melanoma, radiculopathy, myelofibrosis, glioblastoma, gliosarcoma, malignant gliomas, myelogenous leukemia, refractory plasma cell neoplasm, chronic myelomonocytic leukemia, follicular lymphoma, ciliary body and chronic melanoma, iris melanoma, recurrent interocular melanoma, extraocular extension melanoma, solid tumors, T-cell lymphoma, erythroid lymphoma, monoblastic and monocytic leukemia; myeloid leukemia, brain tumor, meningioma, spinal cord tumors, thyroid cancers, mantle cell lymphoma, non-small cell lung cancer, ovarian cancer, prostate cancer, renal cell cancer, myelofibrosis, Burkitt's lymphoma, Hodgkin's lymphoma, large cell lymphoma, or Waldenstrom's macroglobulinemia.

In another embodiment, the disease is selected from myelodysplastic syndromes or multiple myeloma.

Identifying a patient in need of such treatment can be in the judgment of a patient or a health care professional and can be subjective (e.g. opinion) or objective (e.g. measurable by a test or diagnostic method).

In another embodiment, the above method of treatment comprises the further step of co-administering to the patient one or more second therapeutic agents. The choice of second therapeutic agent may be made from any second therapeutic agent known to be useful for co-administration with lenalidomide. The choice of second therapeutic agent is also dependent upon the particular disease or condition to be treated. Examples of second therapeutic agents that may be employed in the methods of this invention are those set forth above for use in combination compositions comprising a compound of this invention and a second therapeutic agent.

In one embodiment, the second therapeutic agent and the corresponding disease for which the second therapeutic agent is co-administered with a compound of this invention is set forth in Table 1 below.

TABLE 1

Second Therapeutic Agents for Various Diseases or Conditions

| Second Therapeutic Agent | Disease or Condition |
|---|---|
| Irinotecan | Multiple myeloma |
| Aldesleukin | Tumor treatment |
| P38 MAP kinase inhibitor | Multiple myeloma |
| 24-hydroxylase inhibitor | Cancer |
| Aminopteridinone | Cancer |
| IGF-1R inhibitor | Tumor treatment |
| COX-2 inhibitor | Neoplasia |
| Nucleobase oligomer | Neoplasia |
| Chlorpromazine | Neoplasia |
| Pemetrexed | Non-small cell lung cancer |
| Topotecan | ovarian and primary peritoneal carcinoma |
| doxorubicin | ovarian and primary peritoneal carcinoma |
| doxorubicin and dexamethasone | multiple myeloma |
| Bortezomib | multiple myeloma |
| Gemcitabine | pancreatic cancer |
| DTIC (Dacarbazine) | Malignant myeloma |
| Bortezomib | multiple myeloma |
| DVd (Doxil, Vincristine and Decadron) | multiple myeloma |
| azacitidine | myelodysplastic syndrome |
| radiation therapy | glioblastoma, gliosarcoma, malignant glioma |
| Rituximab | chronic lymphocytic leukemia, follicular lymphoma, mantle cell lymphoma, Waldenstrom's Macroglobulinemia |
| prednisone | Myelofibrosis |
| docetaxel | solid tumor |
| melphalan | multiple myeloma |
| Bortezomib and dexamethasone | multiple myeloma |

The term "co-administered" as used herein means that the second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention comprising both a compound of the invention and a second therapeutic agent to a patient does not preclude the separate administration of that same therapeutic agent, any other second therapeutic agent or any compound of this invention to the patient at another time during a course of treatment.

Effective amounts of these second therapeutic agents are well known to those skilled in the art and guidance for dosing may be found in patents and published patent applications referenced herein, as well as in Wells et al, eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the invention where a second therapeutic agent is administered to a patient, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

In yet another aspect, the invention provides the use of a compound of Formula I alone or together with one or more of the above-described second therapeutic agents in the manufacture of a medicament, either as a single composition or as separate dosage forms, for treatment in a patient of a disease, disorder or symptom set forth above.

Another aspect of the invention is a compound of Formula I for use in the treatment in a patient of a disease, disorder or symptom thereof delineated herein.

EXAMPLES

Example 1

Synthesis of (S)-3-(Amino-$d_2$)(piperidine-1,3,4,4,5,5-$d_6$)-2,6-dione deuterium chloride salt (24).

Intermediate 24 was prepared as outlined in Scheme 3 below. Details of the synthesis follow.

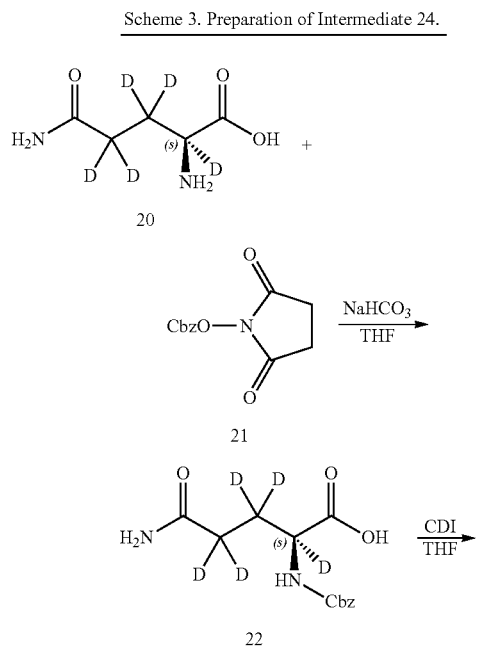

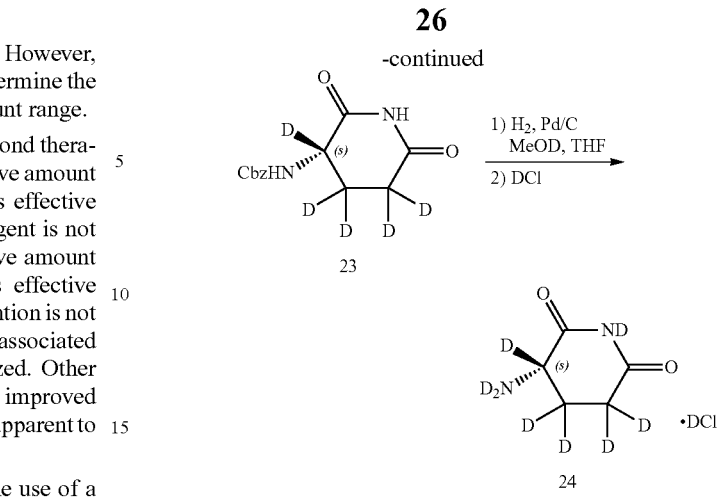

Synthesis of (S)-5-Amino-(2-benzyloxycarbonylamino)-5-oxo-(2,3,3,4,4-$d_5$)pentanoic acid (22). Deuterium oxide (Cambridge Isotopes, 99 atom % D, 2.5 mL) was added to a suspension of L-glutamine-2,3,3,4,4-$d_5$ 20 (CDN Isotopes, 99.2 atom % D, 2.58 g, 17.09 mmol, 1.0 equiv) in tetrahydrofuran (150 mL) and the suspension was stirred for 0.25 hours (h). N-(Benzyloxycarbonyloxy)succinimide 21 (8.93 g, 35.88 mmol, 2.1 equiv) was added in one portion and the resulting mixture was stirred at room temperature for 42 hours. The mixture was concentrated under reduced pressure to remove most of the tetrahydrofuran, and saturated aqueous sodium bicarbonate solution (30 mL) was added to the residual oily solid. The mixture was diluted with water (10 mL) and washed with ethyl acetate (50 mL). The organic phase was discarded. The aqueous phase was acidified to pH 1-2 with a mixture of concentrated hydrochloric acid and ice. The mixture was extracted with ethyl acetate (5×50 mL). The combined organic phases were washed with brine (50 mL), dried over sodium sulfate, filtered and concentrated under reduced pressure to give a gel-like residue. The residue was dissolved in methanol (30 mL), the solution was diluted with toluene (30 mL) and the mixture was concentrated under reduced pressure. The residue was redissolved in methanol (30 mL), and the resulting solution was diluted with toluene (30 mL) and then seeded prior to concentration. The mixture was concentrated under reduced pressure at room temperature to give a white solid. The solid was suspended in 1:1 toluene/heptane (60 mL) and concentrated under reduced pressure. The resulting white solid was dried under high vacuum for 1.75 hours to give 3.80 g (78%) of 22.

Synthesis of (S)-Benzyl 2,6-dioxo(piperidin-3,4,4,5,5-$d_5$)-3-ylcarbamate (23). A mixture of 22 (3.27 g, 11.47 mmol, 1.0 equiv) and N,N'-carbonyldiimidazole "CDI" (3.60 g, 13.72 mmol, 1.2 equiv) in tetrahydrofuran (75 mL) was heated at reflux for 8.5 hours. A clear solution formed after approximately 0.75 hours and a yellow color developed gradually over the course of the reaction. The reaction mixture was cooled to room temperature and stirred overnight. The reaction mixture was concentrated under reduced pressure to remove most of the tetrahydrofuran and the residual yellow oil was partitioned between ethyl acetate (150 mL) and 1N hydrochloric acid (100 mL). The organic phase was washed with brine (75 mL), dried over sodium sulfate, filtered and concentrated under reduced pressure to give a colorless oil that slowly crystallized. The crude product was purified on an Analogix automated chromatography system eluting with a gradient of 25-67% ethyl acetate/heptanes. Product-containing fractions were concentrated under reduced pressure to give 2.41 g (79%) of 23 as a white solid.

Synthesis of (S)-3-(Amino-$d_2$)(piperidine-1,3,4,4,5,5-$d_6$)-2,6-dione, deuterium chloride salt (24). A mixture of 23 and methanol-$d_1$ (Cambridge Isotopes, 99 atom % D, 10 mL) was warmed until all solids dissolved, then cooled to room temperature and concentrated under reduced pressure. The residual solid was redissolved in a mixture of methanol-$d_1$ (10 mL) and tetrahydrofuran (10 mL) and 10% Pd—C (50 mg) was added. The mixture was subjected to hydrogenation at 35-40 psi hydrogen pressure for 2.75 hours. The mixture was filtered through a pad of Celite, which was washed with methanol-$d_1$ (40 mL). A solution of 35% deuterium chloride in deuterium oxide (Aldrich, 99.5 atom % D, 0.75 mL) was added to the combined filtrates. After several minutes, a small amount of white solid formed. The mixture was then concentrated under reduced pressure to give a wet solid. The wet solid was azeotropically dried by concentrating under reduced pressure with toluene (4×25 mL). The resulting white solid was further dried under high vacuum at room temperature for 1.5 hours to give 0.58 g (103%) of 24.

Example 2

Synthesis of Methyl 2-(Bromomethyl-$d_2$)-3-nitrobenzoate 27

Intermediate 27 was prepared as outlined in Scheme 4 below. Details of the synthesis are as follows.

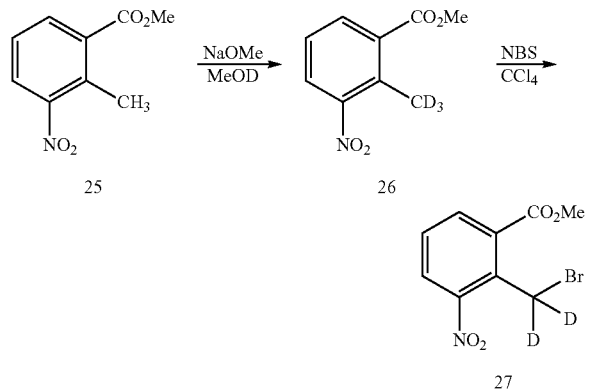

Scheme 4. Preparation of Intermediate 27.

Synthesis of Methyl 2-(Methyl-$d_3$)-3-nitrobenzoate (26). Sodium (0.27 g, 11.7 mmol, 11.7 mol %) was dissolved in methanol-$d_1$ (Aldrich, 99.5 atom % D, 250 mL). Methyl 2-methyl-3-nitrobenzoate 25 (19.5 g, 100 mmol) was added and the mixture was heated at reflux for 25 hours. An aliquot of the reaction mixture was withdrawn and concentrated under a stream of nitrogen. $^1$H NMR of the residual solid showed approximately 88% deuterium incorporation at the 2-methyl group. The mixture was heated at reflux for an additional 18 hours. $^1$H NMR of an aliquot showed approximately 92% deuterium incorporation. The mixture was cooled to room temperature and concentrated under reduced pressure to give a brown solid. This solid was combined with approximately 1.6 g of material (approximately 95% D) from an earlier batch and all of the solids were dissolved in fresh methanol-$d_1$ (200 mL). A solution of sodium (0.27 g, 11.7 mmol) in methanol-$d_1$ (15 mL) was added and the mixture was heated at reflux for 24 hours. $^1$H NMR of an aliquot showed approximately 99% deuterium incorporation. The mixture was cooled to room temperature and concentrated under reduced pressure to give a brown solid. The solid was dissolved in methyl tert-butyl ether (600 mL) and the solution was washed with water (100 mL). The organic phase was separated, washed with water (200 mL), brine (100 mL), dried over sodium sulfate, filtered, and concentrated under reduced pressure to give 19.3 g (88% combined yield) of 26 as an off-white solid.

Synthesis of Methyl 2-(bromomethyl-$d_2$)-3-nitrobenzoate (27). Benzoyl peroxide (25% water) (1.6 g, 4.5 mmol, 5 mol %) was added to a suspension of 26 (17.8 g, 90 mmol, 1.0 equiv) and N-bromosuccinimide (17.8 g, 99 mmol, 1.1 equiv) in carbon tetrachloride (350 mL). The reaction mixture was heated at reflux for 22.5 hours, and then cooled to room temperature. N-Bromosuccinimide (5.3 g, 30 mmol, 0.33 equiv) and benzoyl peroxide (25% water) (0.5 g) were added and the reaction mixture was heated at reflux for 8 hours, cooled to room temperature and stirred overnight. The yellow organic suspension was washed with saturated sodium thiosulfate solution (250 mL), water (200 mL), brine (200 mL), dried over sodium sulfate, filtered, and concentrated under reduced pressure to give 27.9 g of crude product which partially crystallized. The crude product was dissolved in a minimum volume of dichloromethane and adsorbed onto silica gel. The adsorbed material was dry-loaded onto a column of silica gel (400 g) packed in heptanes. The column was eluted with heptanes (2 L), 5% methyl tert-butyl ether/heptanes (2 L), 10% methyl tert-butyl ether/heptanes (2 L) and 20% methyl tert-butyl ether/heptanes (3.5 L). Product-containing fractions were concentrated under reduced pressure and the resulting solid was triturated with hexanes (approximately 100 mL), filtered and dried to give 20.2 g (81%) of 27 as a pale yellow solid.

Example 3

Synthesis of 3-(4-Amino-1-oxo-2,2-$d_2$-isoindolin-2-yl)(piperidine-3,4,4,5,5-$d_5$)-2,6-dione (104)

Compound 104 was prepared as outlined in Scheme 5 below. Details of the synthesis are set forth below.

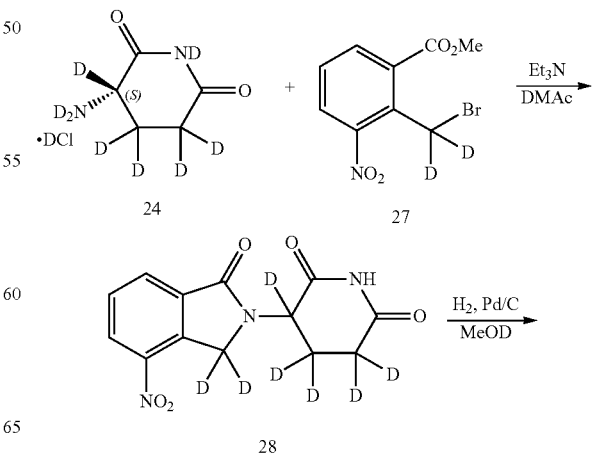

Scheme 5. Preparation of Compound 104.

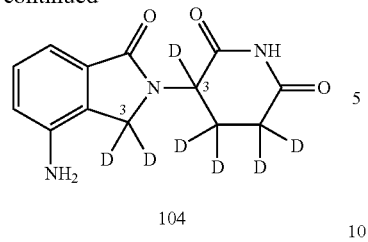

104

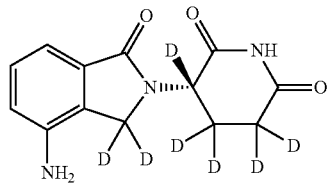

104a

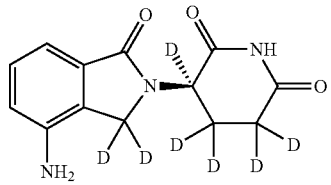

104b

Synthesis of 3-(4-Nitro-1-oxo-3,3-d$_2$-isoindolin-2-yl)(piperidine-3,4,4,5,5-d$_5$)-2,6-dione (28). Triethylamine (1.05 g, 1.45 mL, 10.4 mmol, 2.1 equiv) was added dropwise via syringe to a stirred suspension of 24 (0.86 g, 4.97 mmol, 1.0 equiv) and 27 (1.37 g, 4.37 mmol, 1.0 equiv) in anhydrous N,N-dimethylacetamide (15 mL). The reaction mixture was heated to approximately 85° C. for 1.5 hours. The reaction mixture became dark blue upon heating and a suspension reformed. The reaction mixture was cooled to rt and deuterium oxide (Cambridge Isotopes, 99 atom % D, 10 mL) was added slowly to the reaction mixture. The mixture was stirred for 10 minutes, then the solid was filtered, washed with deuterium oxide (20 mL) and then with methanol-d$_1$ (Cambridge Isotopes, 99 atom % D, 20 mL), and dried to give 1.01 g of 28 as a pale gray solid. $^1$H NMR showed that 28 contained approximately 7-8% H at the 3-position of the piperidinedione ring and approximately 6-7% H at the 3-position of the isoindolinone ring. A portion of the crude product 28 (500 mg) was then suspended in acetonitrile (40 mL), and deuterium oxide (Cambridge Isotopes, 99.8 atom % D, 4 mL) was added followed by triethylamine (0.23 mL, 1.68 mmol). The suspension was heated at reflux for 8 h, cooled to rt and stirred overnight. The solid was filtered, washed with acetonitrile (5 mL), and dried to give 371 mg of an off-white solid. $^1$H NMR showed that recovered 28 contained approximately 3% H at the 3-position of the piperidinedione ring and approximately 2% H at the 3-position of the isoindolinone ring.

Synthesis of 3-(4-Amino-1-oxo-3,3-d$_2$-isoindolin-2-yl)(piperidine-3,4,4,5,5-d$_5$)-2,6-dione (104). Approximately 10 mg of 10% palladium on carbon (approximately 50% wet with deuterium oxide) was added to a suspension of 28 (350 mg) in methanol-d$_1$ (Cambridge Isotopes, 99 atom % D, 350 mL) and the mixture was subjected to an atmosphere of deuterium gas (approximately 50 psi) for 5 hr. The mixture was filtered through a pad of Celite and the pad was washed with methanol-d$_1$ (100 mL). The filtrate was concentrated under reduced pressure to give a white solid with some gummy material present. The crude product was triturated with hot ethyl acetate (approximately 20 mL) and filtered while warm to give 261 mg of 104 as a light tan solid. $^1$H-NMR (300 MHz, DMSO-d$_6$): δ5.42 (s, 1H), 5.44 (s, 1H), 6.79 (d, J=7.9, 1H), 6.91 (d, J=7.0, 1H), 7.19 (dd, J$_1$=7.6, J$_2$=7.6, 1H), 11.02 (s, 1H). $^{13}$C-NMR (75 MHz, DMSO-d$_6$): δ 111.08, 117.04, 126.16, 129.55, 133.04, 144.32, 144.38, 169.62, 172.01, 173.69. HPLC (method: Zorbax 4.6×50 mm SB-Aq 3.5 μm column—gradient method 2-98% ACN+0.1% formic acid over 6.0 min with MSD in ESI positive mode; 0.63 mL/min; wavelength: 254 nm): retention time: 3.99 min; 98.6% purity; MS (M+H): 267.0.

Example 4

Chiral Separation of Compound 104

The enantiomers of Compound 104 were separated via chiral chromatography as described below.

Batches of 104 (25 mg/batch) for injection into the HPLC instrument were dissolved in methanol-D (Cambridge Isotopes, 99 atom % D, 15-17 mL/batch) via sonication. Separation was carried out in 36 injections on a Daicel ChiralPak AD column (20×250 mm, 10 μm) with approximately 1400 μL of 104 solution per injection. Each run was eluted with the isopropanol/hexanes solvent system shown in Table 2 below.

TABLE 2

Solvent System for Chiral HPLC Separation

| Time (min) | Flow Rate (mL/min) | IPA (%) | Hexanes (%) |
|---|---|---|---|
| 0 | 10 | 40 | 60 |
| 2 | 12 | 40 | 60 |
| 25 | 12 | 50 | 50 |
| 27 | 12 | 50 | 50 |
| 28 | 12 | 40 | 60 |
| 33 | 12 | 40 | 60 |

Fractions containing the 1$^{st}$ eluting enantiomer were pooled and concentrated to give 34.2 mg as an off-white solid. Chiral HPLC analysis indicated the 1$^{st}$ eluting enantiomer was >99% ee. HPLC analysis indicated the sample was 95.8% pure. $^1$H NMR showed that the 1$^{st}$ eluting enantiomer contained approximately 2% H at the 3-position of the piperidinedione ring and approximately 2% H at the 3-position of the isoindolinone ring. $^1$H-NMR (300 MHz, DMSO-d$_6$): δ5.41 (s, 2H), 6.79 (d, J=7.9, 1H), 6.91 (d, J=7.3, 1H), 7.18 (dd, J$_1$=7.9, J$_2$=7.3, 1H), 10.99 (s, 1H). HPLC (method: Zorbax 4.6×50 mm SB-Aq 3.5 μm column—gradient method 2-98% ACN+0.1% formic acid over 6.0 min with MSD in ESI positive mode; 0.63 mL/min; wavelength: 254 nm): retention time: 3.91 min; 95.8% purity; Chiral HPLC (method: Chiralpak AD 25 cm column—isocratic method 50% hexane/50% isopropanol for 45 minutes at 0.600 mL/min; Wavelength: 210 nm): retention time: 12.08 min; >99% ee. MS (M+H): 267.3.

Fractions containing the 2$^{nd}$ eluting enantiomer were pooled and concentrated to give 29.1 mg as a light tan solid. Chiral HPLC analysis indicated the 2$^{nd}$ eluting enantiomer was >99% ee. HPLC analysis indicated the sample was >99% pure. $^1$H NMR showed that the 2$^{nd}$ eluting enantiomer contained approximately 2% H at the 3-position of the piperidinedione ring and approximately 2% H at the 3-position of the isoindolinone ring. $^1$H-NMR (300 MHz, DMSO-d$_6$): δ5.41 (s, 2H), 6.79 (d, J=7.9, 1H), 6.91 (d, J=7.6, 1H), 7.18 (dd, J$_1$=7.9, J$_2$=7.3, 1H), 10.98 (s, 1H). HPLC (method: Zorbax 4.6×50 mm SB-Aq 3.5 μm column—gradient method 2-98% ACN+0.1% formic acid over 6.0 min with MSD in ESI positive mode; 0.63 mL/min; wavelength: 254 nm): retention time: 3.91 min; 99.6% purity; Chiral HPLC (method: Chiralpak AD 25 cm column—isocratic method 50% hexane/50% isopropanol for 45 minutes at 0.600 mL/min; Wavelength: 210 nm): retention time: 14.75 min; 99.3% ee. MS (M+H): 267.3.

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention.

We claim:

1. A compound of Formula Ia:

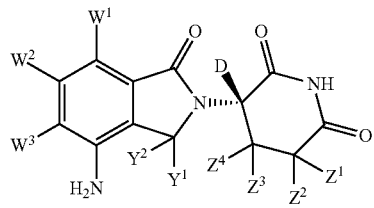

or a pharmaceutically acceptable salt thereof, wherein:
each of $W^1$, $W^2$, and $W^3$ is independently selected from hydrogen or deuterium;
each of $Y^1$ and $Y^2$ is independently selected from hydrogen or deuterium; and
each of $Z^1$, $Z^2$, $Z^3$ and $Z^4$ is independently selected from hydrogen or deuterium;
wherein the compound comprises less than 25% of the other enantiomer, and wherein each position designated as D or deuterium has at least 75% incorporation of deuterium, and wherein any atom not designated as deuterium is present at its natural isotopic abundance.

2. The compound of claim 1, wherein $Z^3$ and $Z^4$ are deuterium; $W^1$, $W^2$ and $W^3$ are simultaneously hydrogen or simultaneously deuterium; $Z^1$ and $Z^2$ are simultaneously hydrogen; and $Y^1$ and $Y^2$ are simultaneously hydrogen.

3. The compound of claim 1, wherein $Z^3$ and $Z^4$ are deuterium; $W^1$, $W^2$ and $W^3$ are simultaneously hydrogen or simultaneously deuterium; $Z^1$ and $Z^2$ are simultaneously hydrogen; and $Y^1$ and $Y^2$ are simultaneously deuterium.

4. The compound of claim 1, wherein $W^1$, $W^2$ and $W^3$ are the same.

5. The compound of claim 4, wherein $W^1$, $W^2$ and $W^3$ are simultaneously hydrogen.

6. The compound of claim 5, wherein $Z^1$, $Z^2$, $Z^3$ and $Z^4$ are the same.

7. The compound of claim 6, wherein $Z^1$, $Z^2$, $Z^3$, $Z^4$ and $Z^5$ are simultaneously deuterium.

8. The compound of claim 7, wherein each Y is simultaneously deuterium.

9. The compound of claim 1, wherein the compound is selected from the group consisting of:

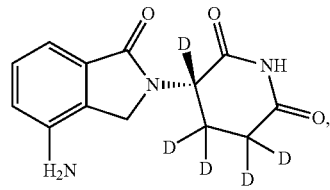

Compound 102a

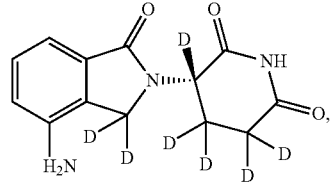

Compound 104a

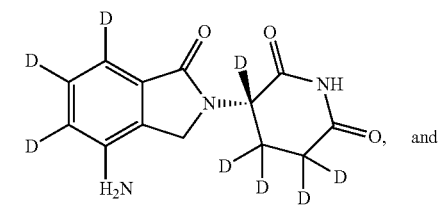

Compound 105a and

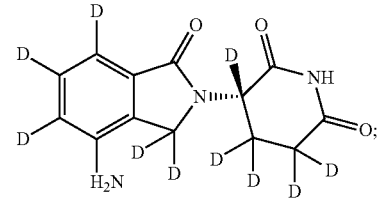

Compound 106a or a pharmaceutically acceptable salt thereof.

10. The compound of claim 1, wherein the compound is selected from the group consisting of:

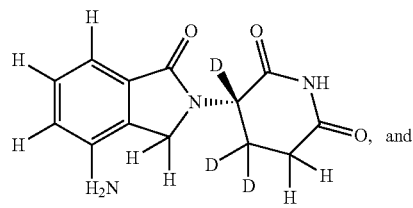

Compound 110a and

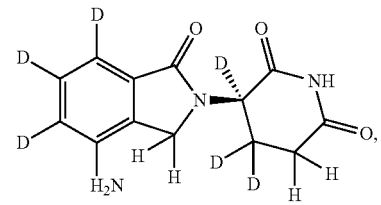

Compound 111a or a pharmaceutically acceptable salt thereof.

11. The compound of claim 1, wherein the compound is selected from the group consisting of:

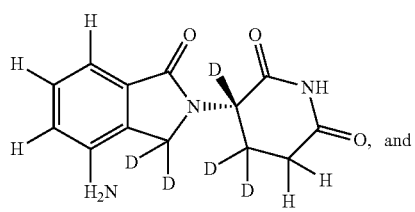

Compound 112a

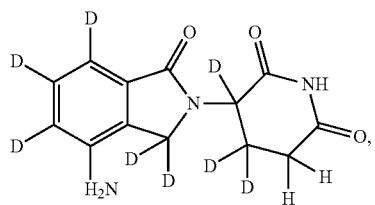

Compound 113a or a pharmaceutically acceptable salt thereof.

12. A pyrogen-free pharmaceutical composition comprising a compound of claim 1, and a pharmaceutically acceptable carrier.

13. The composition of claim 12, additionally comprising a second therapeutic agent selected from pemetrexed, topotecan, doxorubicin, bortezomib, gemcitabine, dacarbazine, dexamethasone, biaxin, doxil, vincristine, decadron, azacitidine, rituximab, prednisone, docetaxel, melphalan, and combinations thereof.

14. A method of treating a disease or condition selected from myelodysplastic syndromes, multiple myeloma, Non-Hodgkins lymphoma; chronic lymphocytic leukemia, amyloidosis, malignant gliomas, chronic myelomonocytic leukemia, follicular lymphoma, myeloid leukemia, mantle cell lymphoma, non-small cell lung cancer, Hodgkin's lymphoma, large cell lymphoma, and Waldenstrom's macroglobulinemia in a patient in need thereof, the method comprising the step of administering to the patient a composition of claim 12.

15. The method of claim 14, wherein the disease is selected from myelodysplastic syndromes and multiple myeloma.

16. The compound of claim 1, wherein the compound comprises less than 10% of the other enantiomer.

17. The compound of claim 1, wherein the compound comprises less than 5% of the other enantiomer.

18. The compound of claim 1, wherein the compound comprises less than 2% of the other enantiomer.

19. The compound of claim 1, wherein each position designated as D or deuterium has at least 90% incorporation of deuterium.

20. The compound of claim 1, wherein each position designated as D or deuterium has at least 95% incorporation of deuterium.

21. The compound of claim 1, wherein the compound comprises less than 10% of the other enantiomer and wherein each position designated as D or deuterium has at least 90% incorporation of deuterium.

22. The compound of claim 1, wherein the compound comprises less than 5% of the other enantiomer and wherein each position designated as D or deuterium has at least 90% incorporation of deuterium.

23. The compound of claim 1, wherein the compound comprises less than 2% of the other enantiomer and wherein each position designated as D or deuterium has at least 95% incorporation of deuterium.

* * * * *

UNITED STATES PATENT AND TRADEMARK OFFICE
CERTIFICATE OF CORRECTION

PATENT NO. : 9,045,453 B2
APPLICATION NO. : 13/107873
DATED : June 2, 2015
INVENTOR(S) : Roger D. Tung Page 1 of 1

It is certified that error appears in the above-identified patent and that said Letters Patent is hereby corrected as shown below:

Claims

At column 32, claim number 10, line numbers 55 to 63, please delete

" 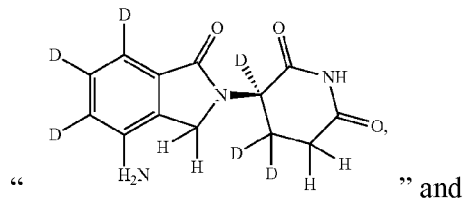 " and replace with -- 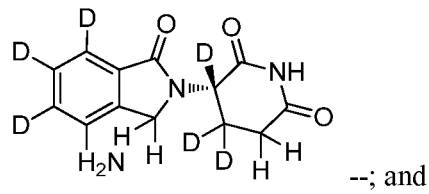 --; and

At column 33, claim number 11, line numbers 10 to 19, please delete

" 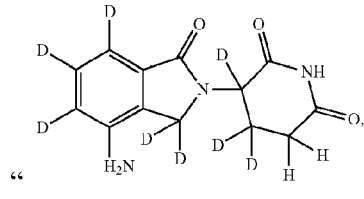 " and replace with -- 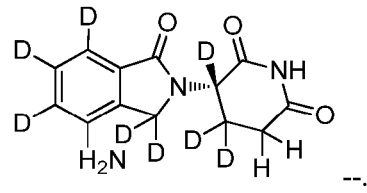 --.

Signed and Sealed this
Twenty-ninth Day of December, 2015

Michelle K. Lee
*Director of the United States Patent and Trademark Office*